(12) United States Patent
Etches et al.

(10) Patent No.: US 6,861,572 B1
(45) Date of Patent: Mar. 1, 2005

(54) PRODUCTION OF PROTEINS IN EGGS

(75) Inventors: Robert J. Etches, San Mateo, CA (US); Mansoor Mohammed, Houston, TX (US); Sherie Morrison, Los Angeles, CA (US); Letitia A. Wims, Culver City, CA (US); Kham M. Trinh, Al Hambra, CA (US); Alan G. Wildeman, Guelph (CA)

(73) Assignee: Origen Therapeutics, Inc., Burlingame, CA (US)

( * ) Notice: Subject to any disclaimer, the term of this patent is extended or adjusted under 35 U.S.C. 154(b) by 0 days.

(21) Appl. No.: 09/486,215

(22) PCT Filed: Aug. 21, 1998

(86) PCT No.: PCT/CA98/00792

§ 371 (c)(1),
(2), (4) Date: Jul. 8, 2002

(87) PCT Pub. No.: WO99/10505

PCT Pub. Date: Mar. 4, 1999

Related U.S. Application Data

(60) Provisional application No. 60/065,865, filed on Nov. 14, 1997.

(51) Int. Cl.[7] ..................... A01K 67/027; A01K 67/00; A01K 67/033
(52) U.S. Cl. ................... 800/19; 800/8; 800/13
(58) Field of Search ............... 800/8, 13, 19, 800/3; 536/23.1, 23.4, 23.53; 435/525

(56) References Cited

U.S. PATENT DOCUMENTS

| | | | |
|---|---|---|---|
| 5,080,895 A | | 1/1992 | Tokoro |
| 5,162,215 A | * | 11/1992 | Bosselman et al. ...... 435/172.3 |
| 5,420,253 A | | 5/1995 | Emery et al. |

FOREIGN PATENT DOCUMENTS

| | | |
|---|---|---|
| WO | WO 94/20608 | 3/1994 |
| WO | WO 97/08307 | 3/1997 |
| WO | WO 97/47739 | 6/1997 |

OTHER PUBLICATIONS

Mohammed et al. Immunotechnology 4:115–125.*
Harvery et al. Nature Biotechnology 19:396–399.*
Chen, H.Y. et al., "Vectors, promoters, and expression of genes in chick embryos," J. Reprod. Fert., Suppl. 41, pp. 173–182, 1990.
Etches, R.J. et al. "Chimeric chickens and their use in manipulation of the chicken genome," Poultry Science, 72:882–889, 1993.
Hassan, J.O. et al. "Effect of Vaccination of hens with an avirulent strain of *salmonella typhimurium* on immunity of progeny challeged with wild–type salmonella strains," Infection and Immunity. vol. 64, No. 3, pp. 938–944, Mar. 1996.
Morrison et al., "Chimeric human antibody molecules: Mouse antigen–binding domains with human constant region domains," Proc. Natl Acad. Sci. USA, vol. 81, pp. 6851–6855, Nov. 1984 Immunology.

* cited by examiner

*Primary Examiner*—Joseph Woitach
(74) *Attorney, Agent, or Firm*—Orrick, Herrington & Sutcliffe LLP

(57) ABSTRACT

Methods for preparing recombinant proteins, such as antibodies, in eggs are described. The method offers advantages over existing systems for preparing recombinant proteins including high yield, low cost and compatibility with animal protection regulations. In addition, since eggs are edible food sources the recombinant protein does not have to be isolated from the egg.

10 Claims, 5 Drawing Sheets

A

B

A

B

A

B

PRODUCTION OF PROTEINS IN EGGS

RELATED INFORMATION

This application claims priority to PCT 98/00792, filed on Aug. 21, 1998 and to U.S. application No. 60/065,865, filed Nov. 14, 1997.

FIELD OF THE INVENTION

The invention relates to a method for the production of recombinant proteins in eggs; an expression system for the delivery of the recombinant proteins to eggs; eggs containing the recombinant protein and transgenic non-human egg-laying animals that produce the recombinant proteins.

BACKGROUND OF THE INVENTION

Biotechnology has allowed the improved production of proteins that have many important medical applications such as the diagnosis and therapy of disease. Unfortunately many of the existing methods for producing recombinant proteins are prohibitive due to the high cost for the large scale production and purification of the proteins.

Antibody molecules are one type of protein that have been prepared using biotechnology. Antibodies (or immunoglobulins) are highly specific tools useful in both the therapy and diagnosis of various diseases and pathogens. Briefly, an intact antibody or immunoglobulin molecule consists of 2 heavy (H) and 2 light chains (L), each having a constant region at the carboxy terminus and a variable region at the amino terminus. Several constant region isotypes have been identified for human immunoglobulins, two for the light chain (kappa and lambda) and five for the heavy chain (alpha, gamma, delta, epsilon and mu). As the name denotes, the sequence of the variable regions varies in each immunoglobulin molecule. The variable region contains the antigen binding site and thus determines the antigen specificity of the immunoglobulin molecule.

When immunizing humans, it is desirable to use human antibodies in order to avoid an immune reaction against the immunizing antibodies. However, due to practical and ethical considerations it has not been possible to prepare large quantities of human antibodies from a human source. Although human Igs derived from serum or breast milk have demonstrated efficacy, the high cost and limited supply of human products preclude their widespread application. In order to decrease the immune response against non-human antibody preparations, chimeric or humanized antibodies have been prepared. Chimeric antibodies are genetically engineered so that the constant region of the antibody is derived from a human antibody and the variable region is derived from the immunized, generally non-human, host. The variable region is usually derived from an antibody isolated from a rodent that has been immunized with the desired antigen.

One area where antibodies are useful is in the treatment of enteric infections. Enteric infections resulting in diarrhea, dysentery or enteric fever constitute a huge public health problem with more than a billion episodes of disease and several million deaths annually in the developing countries. Rotaviruses are one major cause of infectious gastroenteritis in infants and young children in both developed and developing countries. Enterotoxigenic *Escherichia coli* (ETEC) are another major causative agent and result in over 600 million cases of diarrhea worldwide annually. ETEC disease is initiated by consumption of contaminated food or water. Bacteria transit to and colonize the upper small bowel and produce heat stable and/or heat labile enterotoxins. Both types of pathogen should be susceptible to treatment of antibodies targeted to the mucosal surface.

SUMMARY OF THE INVENTION

The present invention relates to a method for the preparation of proteins in eggs. Broadly stated, the present invention provides a method of preparing a recombinant protein in an egg comprising expressing the protein in an egg-laying mammal under conditions suitable for the expression of the protein and delivery of the protein into the egg.

The recombinant protein may be expressed in the animal and delivered to the egg using an expression system that contains a DNA sequence encoding the recombinant protein and necessary regulatory regions to provide for expression of the recombinant protein. When the recombinant protein does not normally accumulate in the egg, the expression system will also contain a second DNA sequence which can target or deliver the protein to the egg of an egg-laying animal.

The second DNA may encode a regulatory region derived from an egg specific gene that can target the expression of the recombinant protein to the egg. Alternatively, the second DNA sequence may encode a protein or peptide that can bind to a receptor on the egg resulting in the uptake of the recombinant protein into the egg.

The present inventors have demonstrated that immunoglobulin proteins can be expressed in an egg-laying mammal and transported to the egg. In particular, the present inventors have found that the constant region from a human immunoglobulin protein can bind to an avian oocyte and be internalized into the yolk.

In one embodiment, the present invention relates to the preparation of a recombinant antibody molecule in a fowl egg. In a preferred embodiment, the present invention relates to the preparation of humanized antibodies in chicken eggs.

The term "humanized antibody" as used herein means an immunoglobulin or antibody molecule that contains a human constant region. The humanized antibody may be chimeric and contain the variable region from a non-human such as a chicken, mouse, etc. The antibody may also be non-chimeric and contain human variable regions. The terms "antibody" and "immunoglobulin" may be used interchangeably throughout the application.

Accordingly, the present invention provides an expression system for delivering a recombinant antibody to an egg comprising (i) a first DNA sequence encoding an immunoglobulin constant region (ii) a second DNA sequence encoding an immunoglobulin variable region and (iii) a regulatory region sufficient to provide for expression of the antibody. Preferably, the constant region is derived from a human immunoglobulin.

The finding by the present inventors that an immunoglobulin protein can bind to and be taken up by an egg allows the delivery of any recombinant protein to an egg by preparing a fusion protein containing (a) a sufficient portion of an immunoglobulin protein to allow for binding and uptake into the egg coupled to (b) the recombinant protein of interest. Accordingly, the present invention provides an expression system for delivering a recombinant protein to an egg comprising (a) a first DNA sequence encoding the recombinant protein operably linked to (b) a second DNA sequence encoding a portion of an immunoglobulin molecule sufficient to bind to the egg and result in the uptake of the recombinant protein. In a specific embodiment, the second DNA sequence is derived from a gene encoding an immunoglobulin constant region.

The above described expression systems may be introduced into an egg-laying animal using a variety of techniques. In one embodiment, the expression system may be introduced directly into the egg-laying animal where the recombinant protein will be expressed and delivered to the egg.

In another embodiment, the expression system may be transfected in culture into a host cell. The host cell can be injected into the egg-laying animal where the recombinant protein will be secreted. The host cell is preferably of the same species as the egg-laying animal. In a specific embodiment, the host cell is an avian cell line. When the recombinant protein is an antibody, the avian cell line is preferably a lymphoid cell line, more preferably an immortalized B cell line such as DT40 or a v-rel transformed B cell line.

In a another embodiment, the expression vector may be delivered to the egg by preparing a transgenic egg-laying animal that expresses the recombinant protein as a fusion protein with a protein or peptide that delivers the protein to the egg, if necessary. Preferably the animal is a fowl, the recombinant protein is an antibody such as a humanized antibody.

The present invention includes an egg preparation containing a recombinant protein as well as all uses of the egg preparation for example in the diagnosis, prevention and treatment of various diseases. The egg preparation can be used directly or the recombinant protein can be further isolated and purified from the egg.

In one embodiment, the antibodies are useful in the prevention and treatment of enteric infections.

The present invention may also be used to prepare pathogen-free eggs by preparing a recombinant antibody specific for the pathogen in the eggs of the animal. Accordingly, the present invention provides a method of preparing an egg that is free of a particular pathogen comprising:

(a) introducing an antibody specific for the pathogen into an egg-laying animal; and (b) allowing the animal to lay an egg wherein the egg is substantially free of the pathogen.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Figure 1:
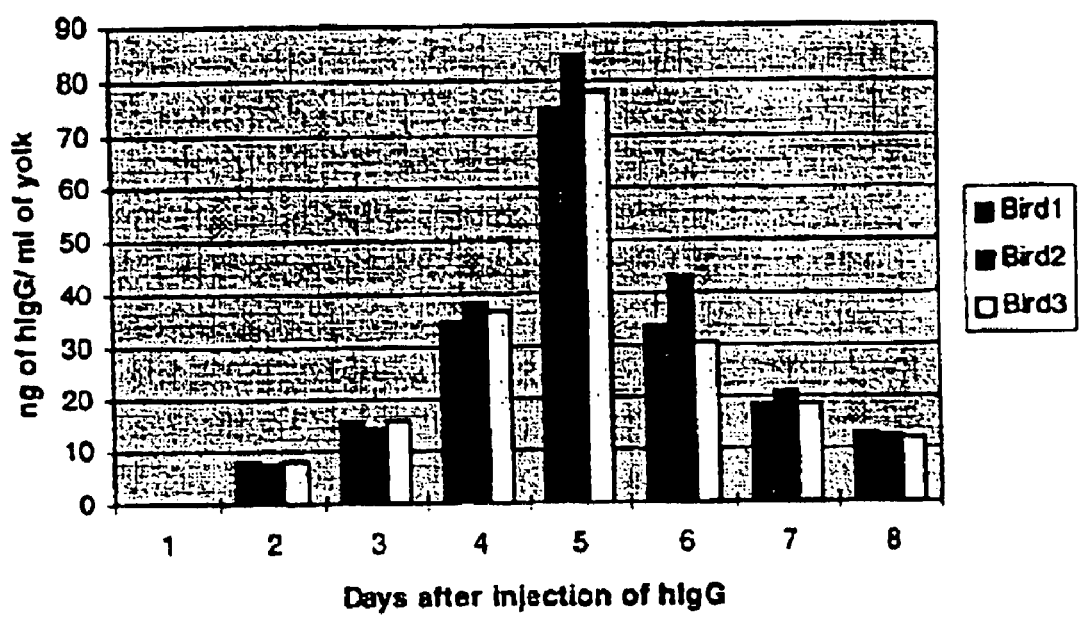
FIG. 1 is a graph showing the concentration hIgG per ml of yolk in eggs versus time.

Broadly stated, the present invention provides a method of preparing a recombinant protein in an egg comprising expressing the protein in an egg-laying mammal under conditions suitable for the expression of the protein and delivery of the protein into the egg.

The protein may be any protein and can include antibodies, cytokines, hormones, enzymes, antigens for vaccines and diagnostic applications, and therapeutic peptides.

The eggs may be from any egg-laying animal including birds, amphibians, reptiles and fish. Preferably, the eggs are from a fowl such as chicken, turkey or duck. The use of eggs as a source of recombinant proteins offers considerable advantages including compatibility with modern animal protection regulations, cheapness, convenience, sterility and the availability of technology for fractionation of egg yolk and isolation of proteins such as antibodies. Since a single egg can yield approximately 100 mg of antibody, a single hen laying 250 eggs per year can produce 25 g of Ig and a small flock of 10,000 hens can produce 25 kg of immunoglobulin annually. Eggs can be stored at room temperature for several weeks.

1. Expression Systems (a) Immunoglobulins

As hereinbefore mentioned, the present inventors have shown that immunoglobulins can be expressed in egg-laying animals and transported to the egg.

In particular the inventors have shown that human immunoglobulin (Ig)G and IgA can be transported to a chicken egg either when injected directly into the chicken (Example 1) or when a cell line expressing a recombinant IgG or IgA is injected into a chicken (Examples 2 and 3). In addition, the inventors have determined that the portion of the immunoglobulin that is responsible for the binding and uptake of the Igs into the avian egg is in the CH2-CH3 region in the Fc domain of the immunoglobulin protein. The inventors have further determined that the Fc receptor on the avian egg is likely a homologue of the mammalian Fc Receptor neonate (FcRn) which plays a role in the transfer of IgGs across the maternofetal barrier, transcytosis of maternal IgGs and regulation of serum Ig levels in mice (Example 4).

Accordingly, the present invention provides an expression system for delivering a recombinant antibody to an egg comprising (i) a first DNA sequence encoding an immunoglobulin variable region (ii) a second DNA sequence encoding an immunoglobulin constant region and (iii) a regulatory region sufficient to provide for expression of the antibody.

In a preferred embodiment, the present invention relates to the preparation of humanized antibodies in chicken eggs. As defined herein, the humanized antibodies contain at least a human constant region. The constant region can be selected from any of the known constant regions including the kappa and lambda light chains and the alpha, gamma, delta, epsilon and mu heavy chain genes. The variable region may be human or non-human such as avian, ovine, murine or bovine. When the variable and constant regions are from different species then the antibody is termed a "chimeric antibody". Chimeric antibodies may be prepared using techniques known in the art such as described in Morrison et al. Proc. Natl. Acad. Sci. 81:6851–6859, 1984 which is incorporated herein by reference.

The variable region may have specificity for a desired antigen. The desired antigen may be selected from bacteria, viruses, toxins, allergens as well as disease specific antigens including tumor associated antigens. A variable region gene encoding a variable region with a desired antigen specificity may be obtained from a hybridoma producing a monoclonal antibody with the desired antigen specificity. A hybridoma producing an antibody with the desired specificity may also be prepared using techniques known in the art. Briefly, an animal (such as a chicken, mouse or rabbit) may be immunized with the desired antigen and lymphocytes producing the antibodies may be obtained. The lymphocytes may be immortalized by fusion with immortal cells such as myeloma cells to prepare a hybridoma. A hybridoma producing the desired antibody may be selected using techniques known in the art (see for example Kohler and Milstein, Nature 256:495–497, 1975). The desired variable region gene can then be isolated from the hybridoma using known techniques such as polymerase chain reaction (PCR).

Bifunctional antibodies may also be prepared which contain two different variable regions with two different antigen specificities.

The DNA sequences encoding the human constant region can be obtained from available sources or can be isolated from a hybridoma cell line producing an antibody with a human constant region using techniques described above.

Recombinant expression vectors containing the DNA sequence encoding a human constant region and the DNA sequence encoding the desired variable region may be prepared. The vectors will additionally include expression control or regulatory sequences such as a promoter, an enhancer and termination sequences. Preferred regulatory sequences are derived from immunoglobulin genes but additional regulatory regions such as those derived from viruses may be useful. The vector can be selected from a variety of vectors including plasmids, viruses, retroviruses, and adenoviruses.

Pre-formed expression vectors may also be prepared that contain the DNA sequence encoding the constant region and the necessary regulatory sequences. A desired variable region DNA sequence can be inserted into the preformed vector in order to prepare an antibody with a desired antigen specificity. The pre-formed vector thus facilitates the preparation of the desired humanized antibody.

(b) Recombinant Fusion Proteins

As hereinbefore mentioned, the present inventors have shown that immunoglobulins bind to and are transported into avian eggs. In addition, the inventors have determined that the portion of the immunoglobulin that is responsible for the binding of the Ig to and uptake in a chicken egg is contained in the CH2-CH3 region of the Fc domain. This finding by the inventors allows the preparation of any recombinant protein in an egg by coupling the desired protein to the sequence of the immunoglobulin sufficient for binding to the egg.

Accordingly, in one aspect, the present invention relates to an expression system for delivering a recombinant protein to an egg comprising (i) a first DNA sequence encoding the recombinant protein operably linked to (ii) a second DNA sequence that encodes a portion of an immunoglobulin protein sufficient to bind to the egg and result in the uptake of the recombinant protein.

The term "portion of an immunoglobulin protein sufficient to bind to the egg" (abbreviated "portion") includes any amino acid sequence derived from an immunoglobulin that can bind to a receptor on an egg and subsequently be transported into the egg. The "portion" preferably binds to the Fc receptor on the egg, more preferably the avian FcRn.

In a specific embodiment, the second DNA sequence is derived from an immunoglobulin constant region. Preferably, the second DNA sequence encodes a portion of the CH2-CH3 region of the constant region domain of the immunoglobulin.

The recombinant protein will be prepared as a fusion protein with the immunoglobulin protein. The recombinant protein may be released form the fusion protein using techniques known in the art.

The expression system will additionally include the necessary regulatory sequences to allow for expression of the recombinant protein such as promoter, enhancer and termination sequences. The expression system may be a viral or a non-viral vector and can be constructed using techniques known in the art. Phagemids are an example of a useful vectors because they can be used either as plasmids or as bacteriophage vectors. Examples of other vectors include viruses such as bacteriophages, baculoviruses and retroviruses, DNA viruses, liposomes and other recombination vectors. The vectors can also contain elements for use in eucaryotic host systems, preferably an avian host system.

One skilled in the art will recognize that the invention includes a method of preparing a recombinant protein using other proteins or peptides that can bind to an egg-specific receptor such as vitellogenin and apolipoprotein B.

2 Delivery and Targeting to Egg

The above described expression systems of the present invention may be introduced into an egg-laying animal using techniques known in the art.

In one embodiment, the expression vector is introduced directly into the egg-laying animal.

Accordingly, the present invention provides a method of preparing a recombinant protein in an egg comprising:

a) introducing an expression system into an egg-laying animal, wherein the expression system comprises (i) a first DNA sequence encoding the recombinant protein operably linked to (ii) a second DNA sequence which can facilitate the delivery of the protein to an egg of an animal;

b) allowing the animal to lay an egg;

c) obtaining the egg containing the recombinant protein; and optionally d) isolating the recombinant protein from the egg.

Preferably, the second DNA sequence encodes a portion of an immunoglobulin protein sufficient to bind to the egg and result in the uptake of the recombinant protein into the egg. More preferably, the second DNA sequence encodes a portion of the CH2-CH3 region of the constant region domain of the immunoglobulin.

In one embodiment, the present invention provides a method of preparing a recombinant antibody in an egg comprising:

a) introducing an expression vector into an egg-laying animal, wherein the expression vector comprises (i) a first DNA sequence encoding an immunoglobulin constant region (ii) a second DNA sequence encoding an immunoglobulin variable region and (iii) a regulatory region sufficient to provide for expression of the antibody;

b) allowing the animal to lay an egg;

c) obtaining the egg containing the recombinant antibody; and optionally d) isolating the recombinant protein from the egg.

The expression systems can be introduced into the cells or tissues of the egg-laying animal by any one of a variety of known methods within the art. Such methods can be found generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor, Mich. (1995), Vectors: A Survey of Molecular Cloning Vectors and Their Uses, Butterworths, Boston Mass. (1988) and Gilboa et al (1986) and include, for example, stable or transient transfection, lipofection, electroporation and infection with recombinant viral vectors.

Introduction of an expression system such as a vector by infection offers several advantages. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

Additional features can be added to the vector to ensure its safety and/or enhance its efficacy. Such features include, for example, markers that can be used to negatively select against cells infected with the recombinant virus. An example of such a negative selection marker is the TK gene described above that confers sensitivity to the anti-viral gancyclovir. Negative selection is therefore a means by which infection can be controlled because it provides inducible suicide through the addition of antibiotic. Such protection ensures that if, for example, mutations arise that produce altered forms of the viral vector or sequence, cellular transformation will not occur. Features that limit expression to particular cell types can also be included. Such features include, for example, promoter and regulatory elements that are specific for the desired cell type.

Recombinant viral vectors are another example of vectors useful for in vivo introduction of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

Transfection vehicles such as liposomes can also be used to introduce the non-viral vectors described above into recipient cells within the inoculated area. Such transfection vehicles are known by one skilled within the art.

In a second embodiment, the recombinant protein may be delivered to the egg by introducing a host cell that has been transformed with an expression system of the present invention into the egg-laying animal. The transformed cell line will secrete the recombinant protein which will be transported to the egg. Preferably the host cell is an avian cell line, specifically a pluripotent or multipotent embryonic cell line, a cell line committed to the germ line or any cell line that can contribute to somatic tissues and the germ line.

Accordingly, the present invention provides a method for preparing a recombinant protein in an egg comprising:

a) introducing a transformed avian cell line that secretes a recombinant protein into an egg-laying animal wherein the avian cell line has been transformed with an expression system comprising (i) a first DNA sequence encoding the recombinant protein and (ii) a second DNA sequence which facilitates the delivery of the protein to an egg of an animal;

b) obtaining the egg containing the recombinant protein; and, optionally c) isolating the recombinant protein from the egg.

In a specific embodiment, the avian cell line secretes a recombinant antibody, preferably a humanized antibody. The avian cell line may be injected into laying hens. The antibodies will be produced in vivo in the hen and will be delivered to and can be obtained from the yolk of the eggs.

Accordingly, the present invention provides a method of preparing a recombinant antibody in a fowl egg comprising:

a) introducing a transformed avian cell line that secretes a recombinant antibody into an egg-laying fowl wherein the avian cell line has been transformed with an expression system comprising (i) a first DNA sequence encoding an immunoglobulin constant region (ii) a second DNA sequence encoding an immunoglobulin variable region and (iii) a regulatory region sufficient to provide for expression of the antibody;

b) obtaining the egg containing the recombinant antibody; and optionally c) isolating the recombinant antibody from the egg.

In a third and preferred embodiment, the recombinant proteins of the present invention may be prepared in an egg-laying animal by preparing a transgenic animal that secretes the recombinant protein which is transported to the eggs. Accordingly, the present invention provides a method of producing a recombinant protein in an egg of an egg-laying animal comprising:

(a) preparing a transgenic egg-laying animal whose somatic and germ line cells contain an expression system comprising (i) a first DNA sequence encoding a recombinant protein operably linked to (ii) a second DNA sequence that facilitates the delivery of the recombinant protein to the egg;

(b) obtaining the egg from the animal; and (c) optionally, isolating the recombinant protein from the egg.

Preferably, the second DNA sequence encodes a sufficient portion of an immunoglobulin protein to allow for targeting of the recombinant protein to the egg and uptake of the recombinant protein into the egg. More preferably, the second DNA sequence encodes a portion of the CH2-CH3 region of the constant region domain of the immunoglobulin.

In a preferred embodiment, a recombinant antibody may be prepared in a fowl by preparing a transgenic fowl that secretes the antibody, preferably a humanized antibody. Accordingly, the present invention provides a method for preparing a recombinant antibody in an egg of an egg-laying animal comprising:

(a) preparing a transgenic egg-laying animal whose somatic and germ line cells contain an expression system comprising (i) a first DNA sequence encoding an immunoglobulin constant region and (ii) a second DNA sequence encoding an immunoglobulin variable region (iii) a regulatory region sufficient to provide for expression of the antibody; and (b) obtaining the egg from the animal.

To prepare a transgenic animal, an expression system of the invention can be inserted into embryos (such as fowl embryos) using techniques known in the art including microinjection, electroporation, sperm transfection, liposome fusion and microprojectile bombardment. The embryos containing the expression system are then transferred to a surrogate shell. The animals carrying the transgene can be grown to sexual maturity and the presence of the recombinant protein can be analyzed in the eggs of the mature animal.

The invention also includes the transgenic egg-laying animals described herein.

3. Egg Preparations

The present invention also includes the eggs containing the recombinant proteins as well as the use of the eggs in all applications. Since eggs are an edible food source, the recombinant proteins do not have to be isolated or purified from the egg. The eggs containing the recombinant protein can be consumed directly or they can be cooked or incorporated into recipes (such as omelets, shakes, baked goods) prior to consumption.

If desired, the recombinant protein can be isolated from the egg and incorporated into a pharmaceutical formulation prior to administration. For example, the humanized antibodies can be removed from the chicken egg using techniques known in the art (see for example U.S. Pat. No. 5,420,253). The antibodies are generally contained in the yolk of the egg which is separated from the rest of the egg in order to obtain the antibodies. The yolk preparation containing the antibodies or other recombinant protein may be lyophilized for storage. The lyophilized preparation may be reconstituted when ready for use.

The antibodies can be used to treat or detect various diseases or pathogens depending on the specificity of the variable region. For the treatment of disease, the antibodies may be administered alone, conjugated or in combination with other compounds. The antibodies may be conjugated to a toxin in order to facilitate the destruction of the diseased or infected cells once the antibody binds to it. Such conjugated antibodies are known as immunotoxins and may be prepared using techniques known in the art (Thorpe et al., Monoclonal Antibodies in Clinical Medicine, Academic Press, p. 168190, 1982).

The recombinant proteins or antibodies may be prepared in a pharmaceutical composition suitable for administration in vivo. The pharmaceutical composition may contain the protein or antibody in a biologically compatible carrier or diluent or in a carrier system such as liposomes. The protein or antibody composition may be administered in a convenient matter such as by injection, oral administration, inhalation, transdermal application or rectal administration. Depending on the route of administration, the active compound may be coated on to a material to protect the compound from the action of enzymes, acids or other natural conditions which may inactivate the antibody. The composition will contain a therapeutically effective amount of the protein or antibody and will be provided at dosages and periods of time necessary to achieve the desired results.

The antibodies may be used for the in vivo or ill vitro diagnosis or detection of disease. For in vivo diagnostics, the antibodies will be prepared in suitable pharmaceutical formulations as discussed above. The antibodies are also generally labelled with a detectable marker to allow their detection. The detectable markers which may be used include various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-111, I-123, I-125, I131, Re-186, Au-198, Au-199, Pb-203, At-211, Pb-212 and Bi-212. The antibodies may also be labelled or conjugated to one partner of a ligand binding pair. Representative examples include avidin-biotin and riboflavin—riboflavin binding protein. Methods for conjugating or labelling the antibodies discussed above with the representative labels set forth above may be readily performed.

The antibodies may also be used to detect disease or pathogens in vitro using techniques known in the art. The methods rely on the binding interaction between the antibodies an antigenic determinant of a protein specific to the pathogen or disease. Examples of such methods are radioimmunoassays, enzyme immunoassays (e.g. ELISA), immunofluorescence, immunoprecipitation, latex agglutination, hemagglutination, and histochemical tests such as enzyme-linked immunosorbant assay (ELISA), and western blotting.

The antibodies of the present invention may be used to treat enteric infections such as rotavirus infection and enterotoxigenic *Escherichia coli* (ETEC) as these are the major causitive agents of disease in newborns and children. Antibodies may be prepared that contain variable regions that are specific for these pathogens or parts of the pathogens.

The present invention can also be used to prepare pathogen free eggs. For example, an antibody specific for a particular pathogen can be produced in an egg-laying animal and transported to the egg where it will neutralize the particular pathogen. In one embodiment, the antibody may be an anti-*salmonella* antibody and can be used to prepare *salmonella* free eggs.

Consequently, in another aspect, the present invention relates to the preparation of an egg that is free of a particular pathogen comprising:

(a) introducing an antibody specific for the pathogen into an egg-laying animal; and (b) allowing the animal to lay an egg wherein the egg is substantially free of the pathogen.

The following non-limiting examples are illustrative of the present invention:

EXAMPLES

Example 1

Uptake of Human Antibodies in the Chicken Egg

To determine if human IgG (hIgG) is capable of being transported into the developing chicken follicle, three Hyline SC™ hens were each injected with 10 μg of purified hIgG and its presence in egg yolk and egg white assessed by ELISA. Human IgG was first detected in egg yolk on Day 2, with peak levels of up to 89 ng/ml detected on Day 5 (FIG. 1). No hIgG was detected in the thin albumen extracts indicating that the concentration was less than 3.12 ng/ml (the detection limit of the ELISA assay).

Figure 2:
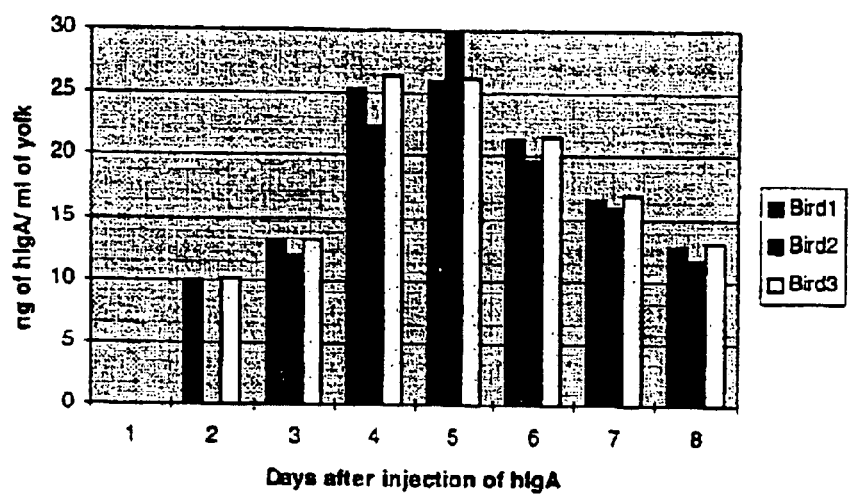
FIG. 2A is a graph showing the concentration of hIgA per ml of yolk versus time.
FIG. 2B is a graph showing the concentration of hIgA per ml of albumen versus time.
Figure 2:
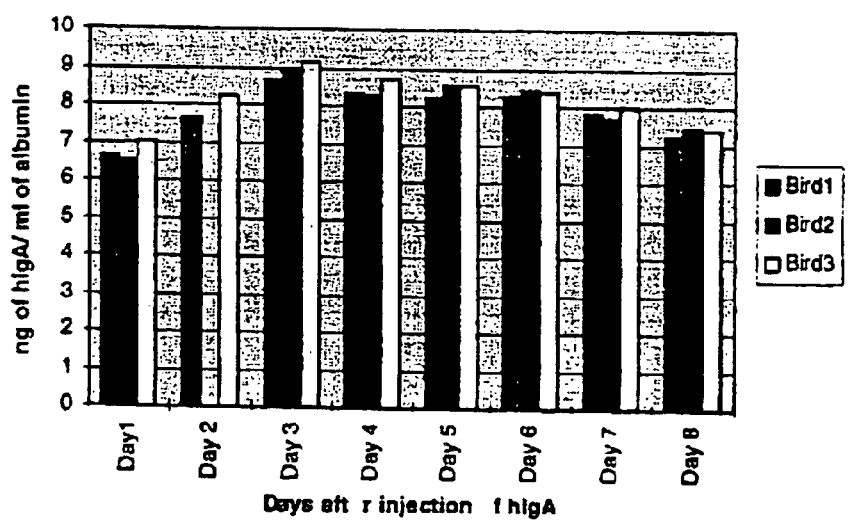

Ten μg of human IgA (hIgA) was also intravenously injected into three Hyline SC™ hens to determine if hIgA was also capable of being deposited into the egg. Human IgA was first detected in the egg yolk on Day 2 with peak levels of up to 33 ng/ml detected on Day 5 (FIG. 2A) which was significantly less than the peak deposition recorded for hIgG (Repeated Measures Analysis, P<0.01). Although hIgG was not detected in egg white extracts, hIgA was. Human IgA was first detected in egg white extracts from Day 1 eggs and remained constant at approximately 8 ng/ml of albumen from Days 2–8 (FIG. 2B).

Example 2
Uptake of Recombinant IgG in Chicken Eggs
Material and Methods
Culture and Transfection of Cell Lines A chicken B lymphoblastoid cell line, DT40, derived from Hyline SC™ chickens (Hyline International, Dallas Center, Iowa) was obtained from Dr. Craig Thompson and used to establish transfected cell lines producing human/mouse chimeric antibodies. Cells were maintained in culture at 1–10× $10^6$ cells/ml in IMDM™ (Gibco BRL) containing 8%(v/v) Bovine Calf Serum (BCS and 2% (v/v) Chicken Serum (CS). Cells (1×$10^7$) were transfected with 20 μg each of linearized heavy chain (chimeric anti-dansyl gamma 1) and light chain (chimeric anti-dansyl light chain with human kappa) by means of electroporation using a Bio-Rad electroporator under optimized electroporation conditions (200V, 960 uF and 1000 msec pulse). Cells were maintained for two days in the above culture media in 96-well microtiter dishes (2.5×$10^4$ cells/well) after which selection medium containing 3 μg/ml mycophenolic acid, 7.5 μg/ml hypoxanthine and 125 μg/ml xanthine was added. Surviving colonies were screened by enzyme-linked immunosorbent assay (ELISA) using dansyl-BSA coated microtiter plates and alkaline phosphatase linked anti-human kappa as the detecting reagents. Strongly positive colonies were then moved into larger dishes for further characterization. Cells from these expanded colonies were labeled by overnight growth in the presence of $^{35}$S-methionine. Following overnight growth, culture supernatant and cytoplasmic lysates were prepared and the contents immunoprecipitated using rabbit anti-human Ig and Staph A (IgSorb). Samples were analyzed on 5% polyacrylamide gels without reduction and on 12% gels following reduction. The position of the bands were determined by autoradiography. Cells from colonies that produced the desired chimeric antibodies were then maintained in culture medium at 1–10×$10^6$ cells/ml.

Production of Tumors in Hyline SC Hens

A transfected DT40 cell line, TAOD 7.4, producing chimeric human anti-dansyl gamma3 was maintained in culture at a concentration of 1×$10^6$ cells/ml in Opti-MEM I™ (Gibco BRL, Burlington) containing 10% Fetal Bovine Serum (FBS). Cells were collected by centrifugation at 300×g for 5 minutes and the culture medium removed. Cells were resuspended at a concentration of 5×$10^7$ cells/ml in Dulbecco's phosphate buffered saline (PBS, Gibco BRL, Burlington, Ontario). A total of 5×$10^6$ cells in 100 μl of PBS was injected subcutaneously into the region between the thigh and body wall of Hyline SC™ hens and tumor development was monitored on a daily basis. Hens were weighed prior to injection and then twice weekly to monitor any fluctuations in weight.

Purification and Analysis of Yolk Antibodies

Eggs were collected from injected hens daily. The yolk was separated from the albumin and antibodies purified from the yolk by means of a gamma Yolk™ preparation kit (Pharmacia Biotech, Morgan Blvd., Quebec). Purified yolk antibody was resuspended in carbonate buffer, pH 9.6, and analyzed for the presence of chimeric human anti-dansyl gamma3 by means of a sandwich antibody ELISA. Immulon™ 96-well microtitre plates were coated overnight at 4° C. with 50 μl of a 5 μg/ml solution of goat anti-human IgG (H+L) (Jackson Immunoresearch, West Grove, Pa., USA) in carbonate buffer, pH 9.6. After overnight incubation the coating mixture was discarded and the plates washed three times with PBS. Plates were then blocked for 1 hr at room temperature by adding 100 μl of blocking buffer (PBS containing 3% (w/v) Bovine Serum Albumin). The blocking buffer was then discarded and the plates washed three times with PBS. Individual yolk antibody preparations or serially diluted standards (Cromopure Human IgG, Jackson Immunoresearch, West Grove Pa., USA) (50 μl) were dispensed into each well and the plate incubated overnight at 4° C. After overnight incubation, the test solutions were discarded and the plates washed three times with PBS. Horseradish peroxidase-conjugated goat anti-human IgG (H+L) (Jackson Immunoresearch, West Grove Pa., USA) (50 UL), at a concentration of 125 ng/ml in blocking buffer, was added to the wells of the plates and incubated at room temperature for 2 hours. The peroxidase-conjugate was then discarded and the plates washed three times with PBS. Horseradish-peroxidase substrate (ammonium acetate-citric acid buffer (pH 5.0) containing 0.05% (w/v) o-phenylenediamine dihyrochloride and 0.05% (v/v) 30% hydrogen peroxide) was then added to each well and the plates incubated in the dark at room temperature for 30 min. Sulphuric acid (50 μl of a 5M solution) was added to each well and the plates were shaken gently on a table top shaker for 10 min. Colour development was then assessed using a Titertek Multiskan™ PLUS ELISA plate reader with a 492 nm filter.

Results

A typical standard curve for the assay of human immunoglobulins in egg yolk is shown in Table 1. Absorbance in the presence of egg yolk is not different from absorbance from a negative control well containing only buffer indicating that egg yolk does not interfere with the assay. The regression coefficient between absorbance at 492 nm and log 10 concentrations of human immunoglobulin (hIg) is 0.99, indicating that the equation y=1.1683x−0.0185 accurately describes the relationship between absorbance and the concentration of hIg.

The effect of yolk in the assay was further examined by constructing a standard curve in presence of yolk extract. As indicated in the graph below, absorbance was unaltered by the presence of yolk at all concentrations of standard in the assay. Absorbance from extracts of yolk from uninjected hens was equal to absorbance at any standard less than 1.56 ng/ml, indicating that concentrations of human Ig less than 1.56 ng/ml could not be detected.

The concentrations of human immunoglobulin in eggs from hen #9185 (Cage #2) are presented in Table 2. This hen was injected with 5 million cells transfected with human IgG3 (TAOD7.4) on day 1. The tumor remained as a small nodule until day 11, at which time hemorrhaging occurred in the region surrounding the tumor. Deposition in yolk was evident in eggs laid on day 13 and 15 although subsequent eggs containing undetectable amounts of hIg.

Discussion

The ELISA for the detection of human immunoglobulin in egg yolk was demonstrated to be sensitive to 1.56 ng/ml, was specific for human immunoglobulin and was reproducible. The recovery of human immunoglobulin from egg yolk was approximately 15% (data not shown).

The presence of a tumor in hen #9185 indicates that DT40 cells will colonize a host chicken to form a somatic chimera. Examination of the concentrations of hIg in yolk from this hen demonstrates that human immunoglobulins are produced by genetically engineered DT40 cells in vivo and sequestered into egg yolk. Since there are approximately 10–15 ml per egg yolk, and the recovery of hIg in the assay was approximately 15%, it is expected that about 625 ng of hIg were deposited in the egg laid by hen #9185 on day 13.

These data provide the rationale for developing a technology for the large-scale production of human immunoglobulins in chicken eggs.

Figure 3:
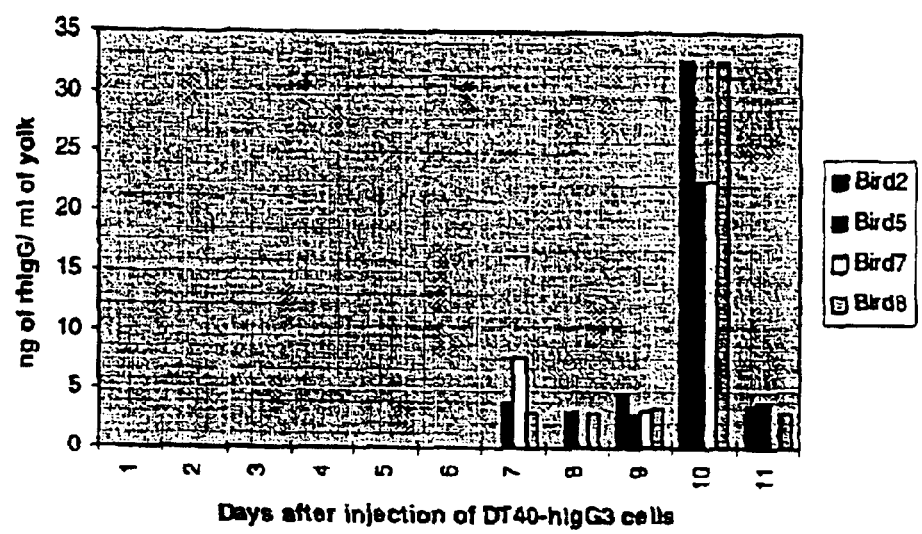
FIG. 3A is a graph showing the mean deposition of rhIgG per ml of yolk versus time.
FIG. 3B shows the best deposition of rhIgG per ml of yolk versus time.
Figure 3:
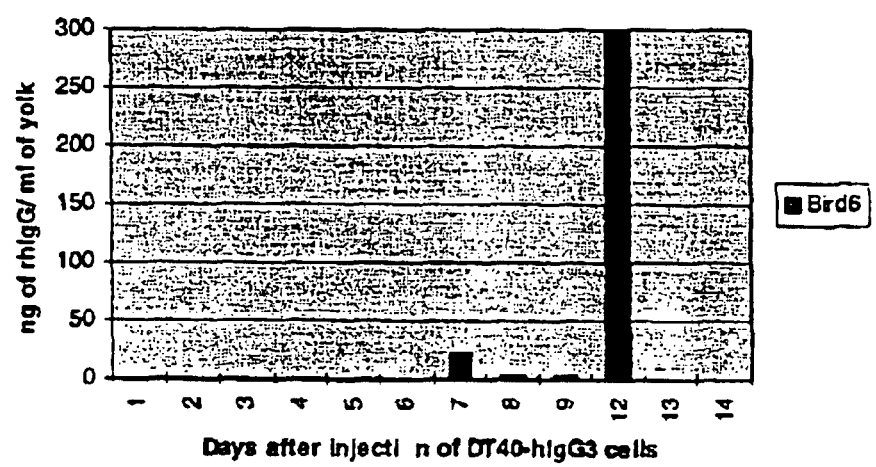

$10^7$ DT40-hIgG3 cells were intravenously injected into 8 Hyline SC™ hens. Of the 8 hens intravenously injected with DT40-IgG3 cells, 3 developed tumors at the site of injection, indicating that some or all of the cells were injected subcutaneously rather than delivered intravenously. Eggs from hens that developed a tumor at the site of injection had very little rhIgG3 in the egg yolk and none in the thin albumen (data not shown). rhIgG3 was first detected in the egg yolk of the remaining 5 hens on Day 7 (FIGS. 3A and 3B). The maximum deposition of rhIgG3 in four of these hens was 33 ng per ml of yolk and occurred in eggs laid on Day 10. One of the hens (Bird 6, FIG. 3B) did not lay an egg on Days 10 or 11, and the egg produced on Day 12, contained 0.3 μg of rhIgG3/ml of yolk. Eggs were not laid by this hen on Days 13 and 14 and no rhIgG3 was detectable in eggs laid on Days 15 and 16.

Figure 4:
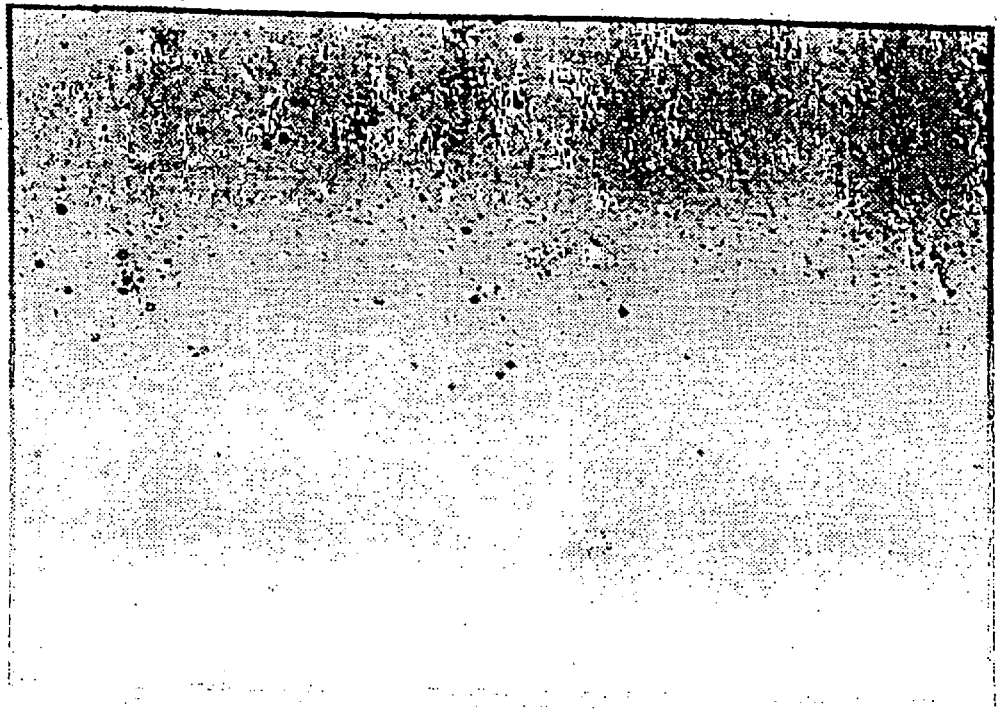
FIG. 4A is a light microscopy of hIgG cells in blood samples taken from hens.
FIG. 4B shows the immunohistochemical staining for hIgG in blood samples taken from hens.
Figure 4:
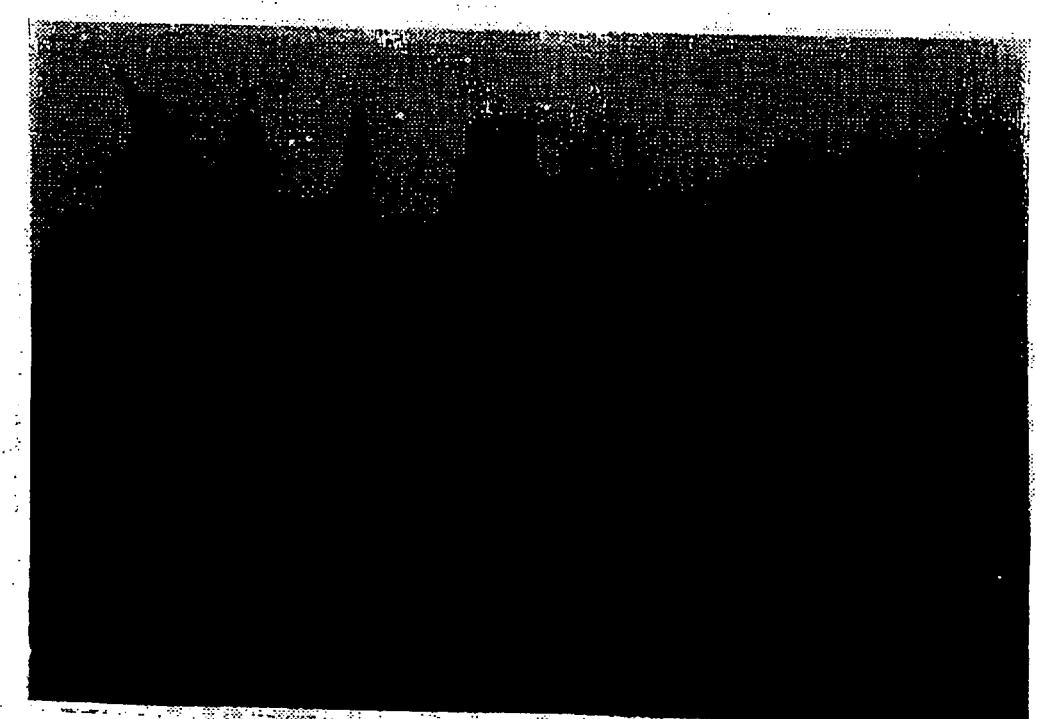

Chicken anti-rhIgG3 was detected in the egg yolk by Day 6 in all hens injected with DT40-IgG3 cells regardless of the presence or absence of a tumor at the site of injection and maximum levels of chicken anti-rhIgG3 in the egg yolk were observed by Day 9 (data not shown). All hens intravenously injected with DT40-IgG3 cells, were euthanized on Day 17. On autopsy, no internal tumors were observed in any of the injected birds. To determine if the DT40-IgG3 cells had been maintained as a leukemia, blood samples were taken from the birds and assessed by both light microscopy and by immunofluomscence staining for the continued presence of DT40-IgG3 cells. No DT40-IgG3 cells were observed in blood samples taken from hens that had developed tumors at the site of injection, though cells derived from these tumors, were successfully reestablished in culture and shown to continue production of rhIgG3 (data not shown). In hens that did not develop tumors at the site of injection, clusters of cells that appeared morphologically similar to the DT40-IgG3 cells were observed in diluted blood samples (FIG. 4A). These were confirmed to be DT40-IgG3 cells by immunohistochemical staining for intracellular hIgG (FIG. 4B).

Example 3
Uptake of Recombinant IgA in Chicken Eggs

Figure 5:
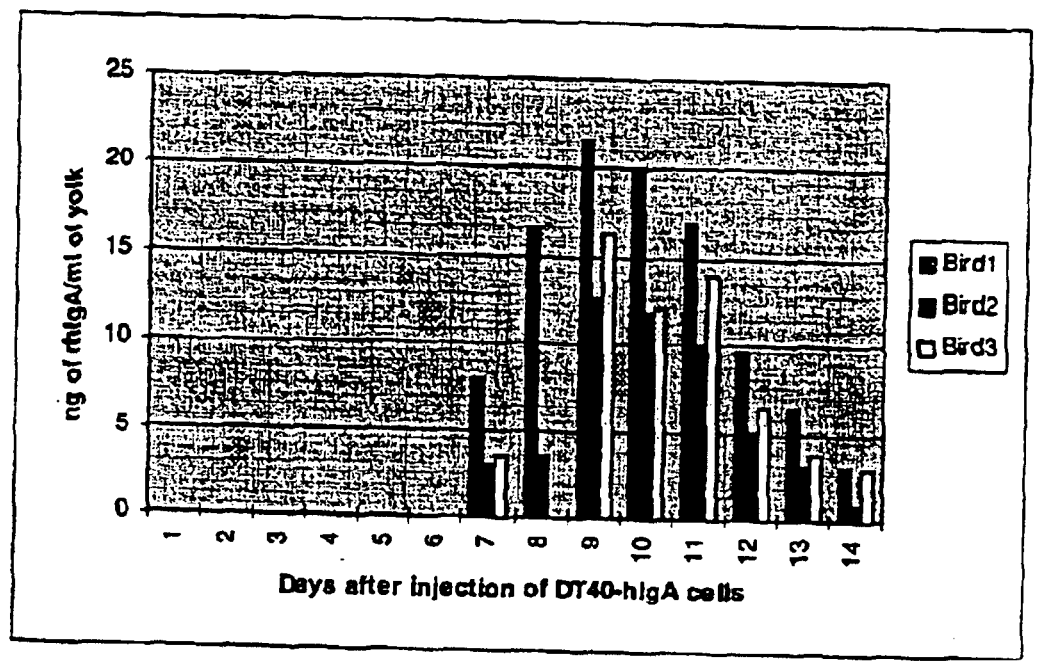
FIG. 5 is a graph showing the concentration of rhIgA per ml of yolk versus time.

Similar to DT4-IgG3 cells, a transfected DT40 cell line, DT40-hIgA, was produced that secretes mouse/human chimeric anti-dansyl a antibodies (rhIgA). In order to demonstrate that a hen with populations of transfected B cells producing rhIgA would transport the rhIgA into the egg, $10^7$ DT40-hIgA cells were intravenously injected into 8 Hyline SC™ hens. Five of the hens injected with DT4-hIgA cells developed tumors at the site of injection. A low level of deposition of the rhIgA into the albumen was detected in all hens injected, but very little deposition of rhIgA was detected in the yolk of hens that developed tumors (data not shown). The 3 hens that did not develop any signs of tumor formation at the site of injection deposited up to 20 ng of rhIgA/ml of yolk by Day 9 (FIG. 5).

Example 4
Characterization of Fc Receptor on Avian Egg

In this study a panel of modified rhIgGs were prepared in an attempt to elucidate the Fc sequences involved in the uptake of Igs into the developing avian oocyte follicle. The inventors are the first to report that the Fc receptor on the developing avian oocyte membrane responsible for transporting IgG into the egg yolk appears to be a homologue of the mammalian FcRn. FcRn is a major histocompatibility complex (MHC) class I-related receptor that plays a role in transfer of IgGs across the maternofetal barrier, transcytosis of maternal IgGs and regulation of serum IgG levels in mice. A homologue has also been found in humans, which appears to perform the same role.

Method and Materials

To facilitate the description of the modifications made to the rhIgGs, a wild-type IgG heavy chain may be represented as V-CH1-H-CH2-CH3. Where V is the variable region, CH_ is the respective heavy chain domain, and H is the hinge region.

A panel of 6 rhIgGs (listed below) were injected into hens essentially as previously described in Example 1.

1. Wild type IgG was used as a positive control.
2. V-CH3 (i.e. missing CH1 through CH2, inclusive).
3. V-CH1-H-CH3 (i.e. missing the CH2 domain).
4. V-CH1-H-CHJ2-*CH3 (i.e. site specific-mutation at CH2–CH3 interface which results in an inability of the rhIgG to bind to FcRn). NB. No deletion.
5. V-CH1-H-CH2-CH3 (i.e. an aglycosylated rhIgG that is incapable of activating complement or binding most known Fc receptors, but retains the ability to bind FcRn). NB. No deletion.
6. V-αCH1-H-CH2-CH3 (i.e. the CH1 constant domain has been swapped with an IgA CH1 domain to demonstrate that regions away from the CH2-CH3 interface can be replaced without affecting binding to the receptor).

Results

The results are shown in Table 3. V-CH3, V-CH1-H-CH3 and V-CH1-H-CH2*-CH3 were not detected in egg yolk samples. V-CH1-H-CH2-CH3 and V-αCH1-H-CH2-CH3 was deposited as efficiently as the control wild-type hIgG.

This example demonstrates that when the CH2-CH3 interface is disrupted by a deletion, rhIgGs are incapable of crossing the avian oocyte membrane. Further, when there are site-specific mutations in the amino acid residues of the CH2-CH3 interface known to interact with FcRn, rhIgGs are also incapable of crossing the avian oocyte membrane. However, the interface between the CH2-CH3 domains has been shown to bind other Fc receptors including Fcγ I–III. The aglycosylated rhIgG, V-CH1-H-CH2-CH3, was chosen to confirm the nature of the oocyte receptor, because aglycosylation of IgGs interferes with complement activation and binding to most Fc receptors but does not interfere with binding to FcRn. Since the aglycosylated rhIgG is deposited into the egg yolk as efficiently as wild-type hIgG, it seems likely that along with the other findings of these experiments, an avian homologue of FcRn is responsible for transport of IgGs across the avian oocyte membrane. These findings should allow the optimization of engineering therapeutic antibodies for production in a transgenic hen model as well as possibly allowing the deposition of any desired protein into the egg yolk by including the sequences required for binding to FcRn.

Example 5
Preparation of Transgenic Chickens

Transgenic chickens which produce recombinant proteins such as humanized antibodies may be prepared. To produce the transgenic chicken, Stage X (40b) embryos may be obtained from unincubated eggs laid by Barred Plymouth Rock hens. Blastodermal cells are harvested by enzymatic digestion of the intercellular matrix and DNA is introduced into the dispersed cells using lipofection reagents as described by Brazolot et al. and Fraser et al. The dispersed cells will then be injected into irradiated stage X recipient embryos in eggs laid by White Leghorn hens as described by Carscience et al. On the fourth day after injection, the injected embryos are transferred to a surrogate shell (109, 109b) which increases the rate of hatching from approximately 10% of injected embryos to approximately 40% of injected embryos (Cochran and Etches, unpublished). At hatch, chimeras can be recognized by the presence of black down of donor (Barred Plymouth Rock) origin and yellow (White Leghorn) down of recipient origin. Hatchlings that show no evidence of incorporation of donor cells are discarded. Comb tissue and blood will be removed on the day of hatch and at 4 weeks of age respectively, and the presence of the DNA sequence coding for the production of the recombinant protein (such as a chimeric antibody) will be determined by PCR. The presence of recombinant protein will be assessed by ELISA conducted on the blood sample taken at 4 weeks of age. Chicks that carry the transgene will be grown to sexual maturity. The deposition of the recombinant protein in developing ova will be assessed by ELISA conducted on extracts from yolks of eggs laid by female chimeras. Both male and female chimeras will be mated and the resulting offspring will be screened by PCR to identify those that contain the construct.

It should be noted that the goal of producing chimeric antibody in eggs will be achieved in chimeras if transfected cells colonize the lymphoid system. A strain of chickens in which the DNA sequences encoding the production of chimeric antibody is incorporated as a Mendelian trait will be derived if the construct is incorporated into the germline. However, even in the absence of germline transmission we will gain significant new information about antibody production in chickens.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Standard Conc. ng/ml | Log 10 of Standard Conc. | Abs. @ 492 nm of Standard Conc. | Average corr. for (−) control | | Abs. @ 492 nm for (−) control | Average (−) control |
|---|---|---|---|---|---|---|
| 0.098 | −1.00877 | 0.079 | 0.085 | −0.008 | 0.1 | 0.08 | 0.09 |
| 0.195 | −0.70997 | 0.101 | 0.109 | 0.015 | | | 0.09 |
| 0.39 | −0.40894 | 0.137 | 0.167 | 0.062 | | | 0.09 |
| 0.78 | −0.10791 | 0.207 | 0.198 | 0.1125 | | | 0.09 |
| 1.56 | 0.193125 | 0.334 | 0.324 | 0.239 | | | 0.09 |
| 3.12 | 0.494155 | 0.637 | 0.578 | 0.5175 | | | 0.09 |
| 6.25 | 0.79588 | 0.959 | 1.017 | 0.898 | | | 0.09 |
| 12.5 | 1.09691 | 1.329 | 1.422 | 1.2855 | | | 0.09 |
| 25 | 1.39794 | 1.499 | 1.393 | 1.356 | | | 0.09 |

TABLE 2

Concentration of human immunoglobulin in yolk from hen #9185 (Cage #2)

| Day | Concentration of hIg (ng/ml yolk) |
|---|---|
| 1 | undetectable |
| 2 | undetectable |
| 3 | undetectable |
| 4 | undetectable |
| 5 | undetectable |
| 6 | undetectable |
| 7 | undetectable |
| 8 | undetectable |
| 9 | undetectable |
| 10 | undetectable |
| 11 | undetectable |
| 12 | no egg |
| 13 | 6.27 |
| 14 | no egg |
| 15 | 3.46 |
| 16 | no egg |
| 17 | undetectable |
| 18 | undetectable |
| 19 | undetectable |
| 20 | undetectable |
| 21 | undetectable |
| 22 | undetectable |
| 23 | undetectable |
| 24 | undetectable |
| 25 | undetectable |
| 26 | undetectable |
| 27 | undetectable |

TABLE 3

Mean deposition of rhIgGs per ml of yolk in eggs laid from hens (n = 5) intravenously injected with 10 μg of each of the panel of rhIgGs.

| | Mean deposition of rhIgGs per ml of yolk (ng/ml) | | | | | |
|---|---|---|---|---|---|---|
| Days After Injection | Wild type IgG | V-CH3 | V-CH1-H-CH3 | V-CH1-H-CH2-*CH# | V-CH1-H-CH2-CH3 | V-αCH1-CH2-CH3 |
| 1 | 0 | 0 | 0 | 0 | 0 | 0 |
| 2 | 4.64 | 0 | 0 | 0 | 3.72 | 3.91 |
| 3 | 8.08 | 0 | 0 | 0 | | |
| 4 | 21.54 | 0 | 0 | 0 | 21.0 | 18.43 |
| 5 | 55.4 | 0 | 0 | 0 | 49.8 | 47.21 |
| 6 | 18.7 | 0 | 0 | 0 | | |
| 7 | 6.96 | 0 | 0 | 0 | | |
| 8 | 3.22 | 0 | 0 | 0 | | |

We claim:

1. An egg-laying chicken whose somatic cells contain an expression system comprising (i) a first DNA sequence encoding a human gamma isotype immunglobulin constant region having a CH2-CH3 region in an Fc domain of the constant region; (ii) a second DNA sequence encoding a human immunoglobulin variable region; (iii) a third DNA sequence comprising an immunoglobulin-gene derived promoter sufficient for expression of the human immunoglobulin constant region in the chicken; wherein the egg-laying chicken produces eggs whose yolk contains human gamma isotype immunoglobulin having a constant region encoded by the first DNA sequence and a variable region encoded by the second DNA sequence.

2. A method of producing a human immunoglobulin protein in an egg of an egg-laying-chicken comprising:

constructing a vector comprising an expression system comprising: (i) a first DNA sequence encoding a human gamma isotype immunoglobulin constant region having a CH2-CH3 region in an Fc domain of the constant region (ii) a second DNA sequence encoding a human immunoglobulin variable region, and (iii) a third DNA sequence comprising an immunoglobulin-gene derived promoter sufficient for expression of the human immunoglobulin constant region in the chicken, and incorporating the vector into a pluripotent chicken cell line, injecting the cell line into a chicken embryo, hatching an egg-laying chicken that produces an egg whose yolk contains human gamma isotype immunoglobulin having a constant region encoded by the first DNA sequence and a variable region encoded by the second DNA sequence.

3. A method according to claim 2 wherein the vector is further comprised of a negative selection marker.

4. A method according to claim 3 further comprising the step of isolating the human immunoglobulin from the egg.

5. A method according to claim 4 further comprising the step of conjugating the immunoglobulin to a toxin.

6. A method according to claim 4 further comprising the step of formulating the human immunoglobulin in a pharmaceutical formulation.

7. The chicken of claim 1 wherein the egg contains at least 3.46 ng of human gamma isotype immunoglobulin per ml of egg yolk.

8. The chicken of claim 1 wherein the expression system is further comprised of an enhancer.

9. The chicken of claim 1 wherein the second DNA sequence encodes a human immunoglobulin variable region that is specific for an antigen.

10. The chicken of claim 9 wherein the antigen is a pathogen.

* * * * *

UNITED STATES PATENT AND TRADEMARK OFFICE
CERTIFICATE OF CORRECTION

PATENT NO. : 6,861,572 B1  Page 1 of 1
APPLICATION NO. : 09/486215
DATED : March 1, 2005
INVENTOR(S) : Robert J. Etches et al.

It is certified that error appears in the above-identified patent and that said Letters Patent is hereby corrected as shown below:

Column 1, line 6, after "RELATED INFORMATION" and before "FIELD OF THE INVENTION": please add:

This invention was made with Government support under Grant No. AI039187 awarded by the National Institutes of Health. The Government has certain rights in this invention.

Signed and Sealed this

Nineteenth Day of January, 2010

David J. Kappos
*Director of the United States Patent and Trademark Office*